United States Patent [19]

Mroczkowski et al.

[11] Patent Number: 5,137,827

[45] Date of Patent: Aug. 11, 1992

[54] DIAGNOSTIC ELEMENT FOR ELECTRICAL DETECTION OF A BINDING REACTION

[75] Inventors: Susan J. Mroczkowski, Franklin; Kenneth A. Siegesmund, Brookfield; Donald E. Yorde, Colgate, all of Wis.

[73] Assignee: Midwest Research Technologies, Inc., Milwaukee, Wis.

[21] Appl. No.: 590,599

[22] Filed: Sep. 25, 1990

Related U.S. Application Data

[63] Continuation of Ser. No. 269,971, Nov. 10, 1987, abandoned, which is a continuation-in-part of Ser. No. 843,982, Mar. 25, 1986, Pat. No. 4,794,089.

[51] Int. Cl.$^5$ .................. C12N 11/14; C12N 11/00; G01N 33/53; G01N 33/563
[52] U.S. Cl. ......................................... 435/288; 435/6; 435/7.4; 435/287; 435/817; 435/174; 435/176; 435/177; 436/149; 436/501; 436/518; 436/524; 436/525; 436/527; 436/73; 436/806; 422/82.02; 422/90; 422/98; 422/186.04; 422/186.15; 422/186.16; 422/186.22; 422/186.26; 204/193
[58] Field of Search ............. 435/4, 5, 180, 182, 435/287, 817, 174, 176, 177; 436/149, 501, 512, 518, 524, 525, 527, 73, 173, 804, 806; 422/68, 90, 98, 174, 186.04, 186.15, 186.16, 186.22, 186.26, 186.27

[56] References Cited

U.S. PATENT DOCUMENTS

| | | | |
|---|---|---|---|
| 4,054,646 | 10/1977 | Giaever | 424/12 |
| 4,072,576 | 2/1978 | Arwin et al. | 195/193.5 R |
| 4,141,687 | 2/1979 | Forrest et al. | 422/81 |
| 4,219,335 | 8/1980 | Ebersole | 23/230 B |
| 4,233,144 | 11/1980 | Pace et al. | 204/195 B |
| 4,238,757 | 12/1980 | Schenck | 357/25 |
| 4,313,734 | 2/1982 | Leuvering | 23/230 B |
| 4,334,880 | 6/1982 | Malmros | 23/230 B |
| 4,444,892 | 4/1984 | Malmros | 435/528 |
| 4,713,347 | 12/1987 | Mitchell et al. | 436/501 |
| 4,775,636 | 10/1988 | Moeremans et al. | 436/518 |
| 4,777,019 | 10/1988 | Dandekar | 422/68 |
| 4,778,767 | 10/1988 | Hummelen | 436/531 |
| 4,794,089 | 12/1988 | Mroczkowski | 436/809 |

FOREIGN PATENT DOCUMENTS 0170375  2/1986  European Pat. Off. .
60-29658  2/1985  Japan .
WO88/09499 12/1988  PCT Int'l Appl. .

OTHER PUBLICATIONS

Laval et al., Enzymatic Electrocatalysis Electrochem. Reg'n of NAD w/Immo. LDH Electrodes, J. Am. Chem. Soc., 106(17), 1984, 4701–4706.
Kricka, Larry J., Ligand–Binder Assays, Marcel Dekker, Inc., N.Y. & Basel, 1985, pp. 88–95.

Primary Examiner—Esther L. Kepplinger
Assistant Examiner—Toni R. Scheiner
Attorney, Agent, or Firm—Foley & Lardner

[57] ABSTRACT

A method is disclosed for detecting the occurrence of a binding or complex-forming reaction between specific substances by utilizing the binding reaction to modify an electrical circuit, and then measuring a change in the electrical state of the circuit. A diagnostic element useful in such a method includes a layer of a biogenic substance, such as an antigen, coated onto a non-conductive base between a pair of electrical conductors superposed on the base. Antibodies which react with the antigen are treated so that they become bound to fine electrically conductive, metallic particles. The electrically conductive particles having antibody bound thereto are then added to the antigen layer deposited on the base and allowed to react therewith. Electrically conductive particles are thereby bound to the base due to the binding reaction between the antigen and antibody to thereby form aggregates of electrically conductive particles which modify the circuit. The method of the invention is highly useful for the detection of antigens and antibodies in the blood serum of a human patient.

20 Claims, 5 Drawing Sheets

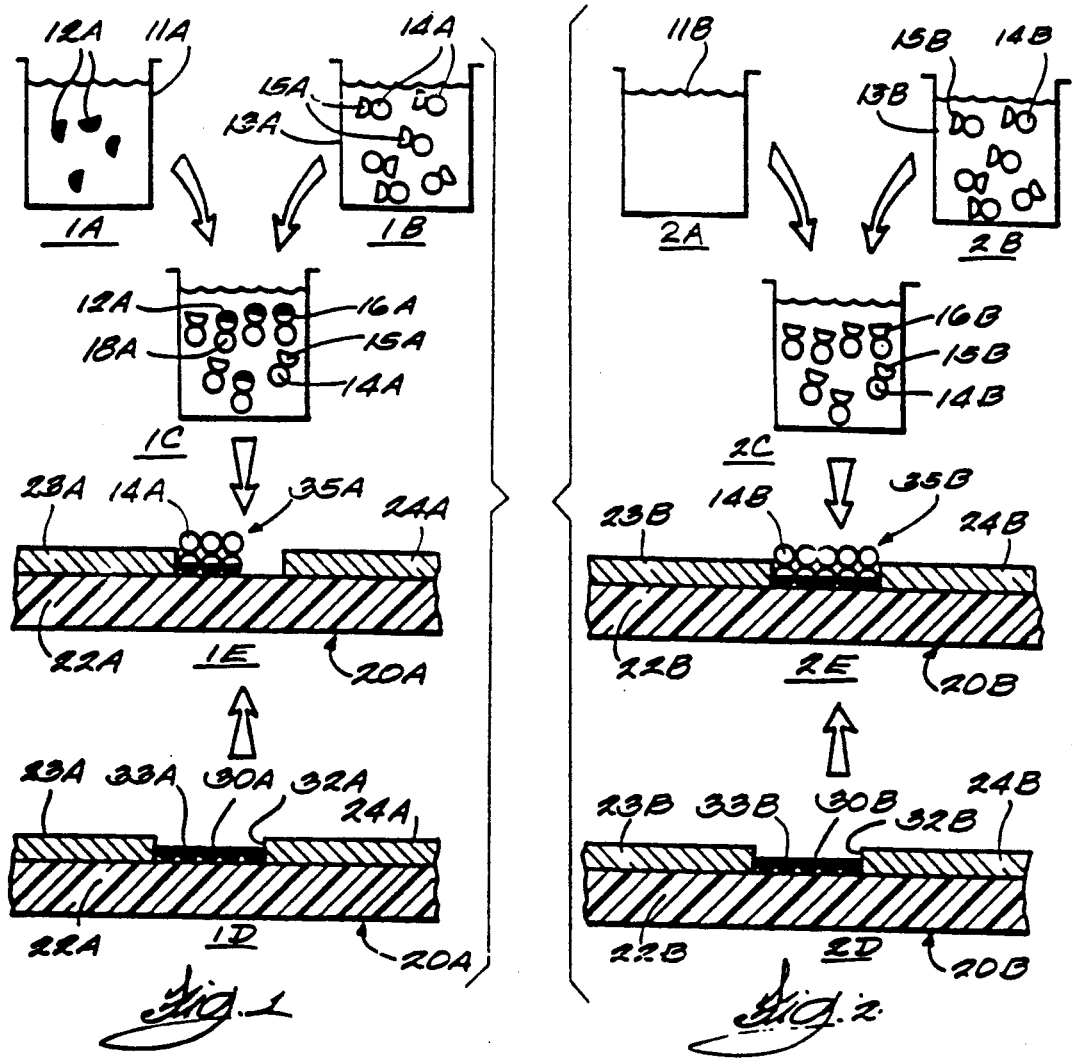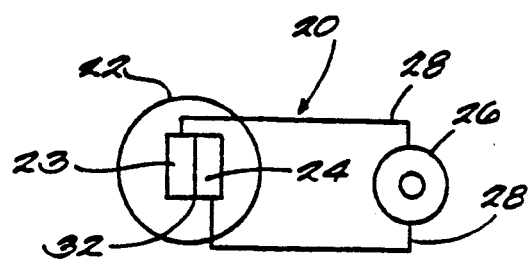

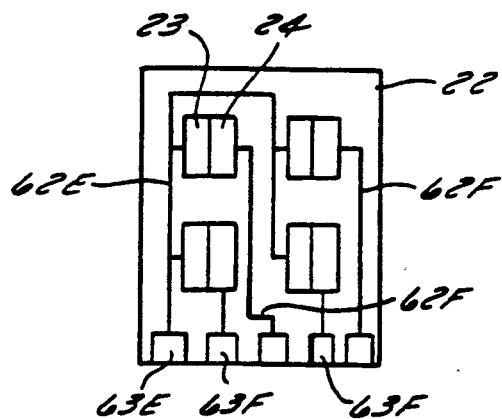
FIG. 9
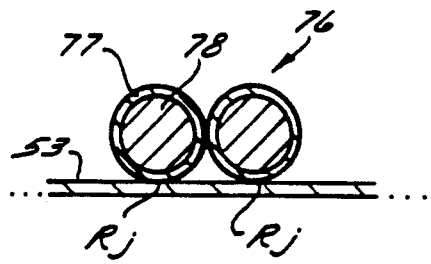
FIG. 10
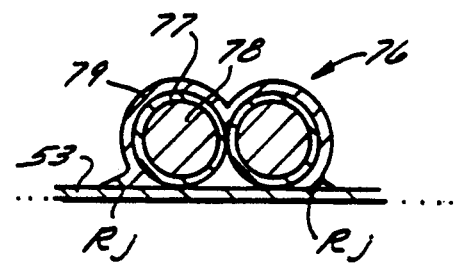
FIG. 11
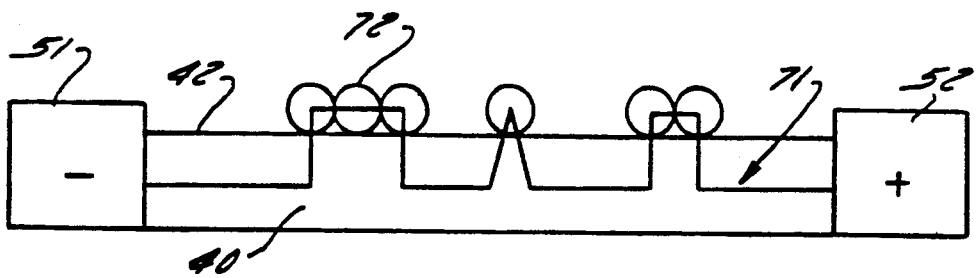
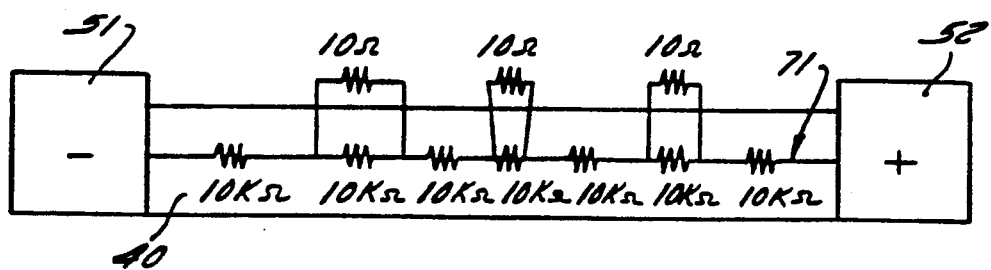
FIG. 12

DIAGNOSTIC ELEMENT FOR ELECTRICAL DETECTION OF A BINDING REACTION

This invention was made with government support under a small business innovation research grant awarded by the National Instituted of General Medical Sciences. The government has certain rights in this invention.

This is a continuation of application Ser. No. 07/269,971 filed Nov. 10, 1988, abandoned, which is a continuation-in-part of U.S. Ser. No. 843,982, filed Mar. 25, 1986, now U.S. Pat. No. 4,794,089, issued Dec. 27, 1988.

FIELD OF THE INVENTION

This invention relates to a diagnostic element for electrically detecting a binding reaction between a pair of chemical substances, particularly biogenic substances such as antigens and antibodies or nucleotides. The invention further concerns a new immunoassay method.

BACKGROUND OF THE INVENTION

It is well known that when a foreign substance such as a bacterium or virus enters a human or animal body, production of antibodies to combat the infection is stimulated by the presence of one or more antigens. Antigens related to invading organisms comprise a foreign substance that comes from the invading organism, such as a piece of bacterium or virus. More generally, an antigen is any substance capable of triggering an immune response. Certain specialized cells of the body contact an antigen and produce antibodies specifically designed for that antigen. When released in the body, such antibodies identify and bind to the antigen, thereby combating the infection. Antibodies are highly specific and will generally bind only to the antigen which stimulated their creation.

When a person has been infected with certain diseases, that person's blood will often contain measurable levels of antigen specific to that disease. To determine whether such an infection is present, an immunodiagnostic test is performed using a sample of the patient's blood. The sample is mixed with a solution known to contain antibodies specific to a certain disease or condition. If an antigen-antibody reaction occurs, the test result is positive, and the antigen is detected. Such a test is typically reversible, i.e., a solution or reagent known to contain a certain antigen can be used to determine whether or not the corresponding antibody is present in a sample. However, the antigen-antibody reaction occurs on a microscopic level and is not readily observable. Thus, all known immunodiagnostic tests provide some type of means for indicating that the antigen-antibody reaction has occurred.

A variety of techniques have been used to detect antigen-antibody reactions. The principal techniques presently in use are enzyme immunoassay, immunofluorescence, and radioimmunoassay. In typical enzyme immunoassay procedures, the antigen-antibody reaction is detected by the formation, by an enzyme, of a colored product from a colorless substrate. Immunofluorescence techniques indicate that a reaction has occurred by emission of small quantities of light which must generally be observed microscopically. Radioimmunoassay utilizes radioactive labeling substances so that occurrence of the antigen-antibody reaction is measured by the presence or absence of small amounts of radioactivity. These known methods are reliable but are slow and tedious.

Recently several types of electrical immunoassay techniques have been developed. One such technique utilizes field effect transistors coated with a layer of antibody in the gate region. If an antigen-antibody reaction occurs, the charge concentration of the transistor changes. Examples of this type of system are given in Schenck U.S. Pat. No. 4,238,757, issued Dec. 9, 1980; Guckel U.S. Pat. No. 4,180,771, issued Dec. 25, 1981; Malmros U.S. Pat. Nos. 4,334,880, issued Jun. 15, 1982 and 4,444,892, issued Apr. 24, 1984, and Japanese Patent fluid containing an analyte to be detected is deposited onto a surface which has been coated with a reagent that binds specifically to the analyte, so that a binding reaction takes place. A tagged reagent is then added which reacts with the analyte-reagent complex or with the reagent to change the electrical reactance of the surface. See Ebersole U.S. Pat. No. 4,219,335, issued Aug. 26, 1980.

Several other methods have been proposed for measuring immunologic reactions electrically. A voltametric immunoassay can be carried by labeling one immunoreactant with an electroactive substance. Pace U.S. Pat. No. 4,233,144, issued Nov. 11, 1980, is illustrative of one such technique. Another method involves sandwiching an antigen-antibody layer between two conductive layers and measuring the electrical capacitance of the resulting laminate Giaever U.S. Pat. No. 4,054,646, issued Oct. 18, 1977, describes such a method. A further type of capacitance-measuring system includes a pair of electrodes coated with a substrate and immersed in a medium containing a material which specifically binds with the substrate, as described in Arwin U.S. Pat. No. 4,072,576. A further method combines change effect signal detection with an enzyme immunoassay technique. Such a method is disclosed by Gibbons U.S. Pat. No. 4,287,300, issued Sep. 1, 1981. The foregoing electrical methods have, however, failed to provide medical practitioners and laboratories with a simple, fast, sensitive, inexpensive and easy-to-use method of performing an immunodiagnostic test.

One aspect of the present invention involves the use of antigen or antibody-labeled colloidal gold particles. In general, "colloidal gold" refers to a suspension of fine gold particles in water or aqueous solution. Preparation of such particles is disclosed by DeMey, et al. U.S. Pat. No. 4,446,238, issued May 1, 1984, and DeMey, et al. U.S. Pat. No. 4,420,558, issued Dec. 13, 1983. The entire contents of both such DeMey patents are incorporated herein by reference. Such colloidal gold preparations have been previously used in immunodiagnostic tests wherein the results are determined optically by observing small amounts of light reflected as a result of the antigen-antibody reaction. The foregoing patents to DeMey disclose a bright field light method of the foregoing type. Silver enhancement has been previously used as a means for staining gold particles. The present invention advantageously employs colloidal gold, optionally with silver enhancement, in a new immunodiagnostic method.

SUMMARY OF THE INVENTION

The present invention provides a method for detecting a binding reaction between a pair of first and second substances, particularly biogenic substances, which specifically bind together. The method of the invention involves bringing the substances together so that the binding reaction between them causes full or partial completion (closing) of an essentially open electrical circuit. The resulting change in the electrical state of the circuit indicates the binding reaction.

According to a further aspect of the invention, a diagnostic element for use in detecting a binding reaction comprises a pair of spaced-apart, electrical conductors, particularly conductive layers, disposed on a substantially non-electrically conductive base. The base may comprise a support having a layer formed thereon which has a high affinity for protein binding and has a moderate to high resistance in comparison to the conductors. The space between the conductors defines a path or channel. One of a pair of substances which bind to each other is deposited on and affixed to the binding layer of the non-conductive base between the conductors, such as on the bottom wall of a channel. Means forming an electrical circuit is connected to each of the conductors so that the channel constitutes a break in the circuit.

As used herein, the term "diagnostic element" refers to the base, conductors, and layer of one of the binding substances, without the means defining the electrical circuit Such a diagnostic element and means forming an electrical circuit can readily be used in conjunction with any suitable means for fully or partially bridging the break in the circuit due to the binding reaction between the pair of substances. One such means involves adhering one of the substances to the surfaces of electrically conductive particles.

BRIEF DESCRIPTION OF THE DRAWING

Preferred exemplary embodiments will hereafter be described in conjunction with the appended drawing, wherein like designations denote like elements, and:

FIGS. 1A, 1B, 1C, 1D and 1E and FIGS. 2A, 2B, 2C, 2D and 2E are schematic diagrams illustrating an immunodiagnostic method according to the invention;

FIG. 3 is a schematic diagram illustrating a reaction detector according to one embodiment of the invention;

FIG. 9 is a plan view of an alternative multiple diagnostic element according to the invention;

FIG. 10 is a schematic diagram of an uncoated bound aggregate according to the invention;

FIG. 11 is a schematic diagram of a coated bound aggregate according to the invention;

FIG. 12 is a schematic diagram of resistive shunting of current according to the invention;

DETAILED DESCRIPTION

Figure 4A:
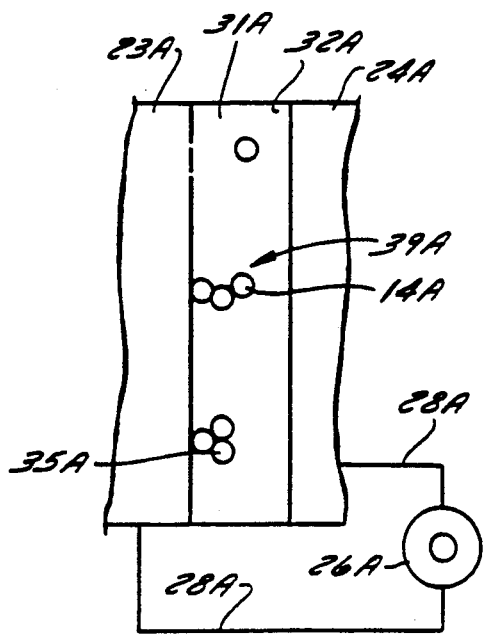
FIGS. 4A and 4B are schematic diagrams showing aggregate formation according to the method of FIGS. 1A-1E and 2A-2E, respectively.

The method of the invention is particularly useful for detecting antigens in the fluids or tissues of humans or animals. Such antigens include drugs, toxins, hormones, allergens, tumor markers, factors, enzymes, steroids, nucleotides and other substances as listed in Huang U.S. Pat. No. 4,327,073, issued Apr. 27, 1982, the entire content of which is incorporated herein by reference Any of the foregoing listed substances can provoke the production of a reactive substance (antibody) which reacts with and binds to the antigen. Accordingly, the method of the present invention is useful for detection of a wide variety of substances which may be present in the living body of a human or lower animal, for example, in drug overdose treatment, where it is desired to quickly determine which drug a patient has taken.

FIGS. 1A-1E schematically illustrate a method for detecting an antigen according to the present invention Referring to FIGS. 1A through 1C, a patient sample 11A (FIG. 1A) such as whole blood, blood serum or urine, containing a particular antigen 12A is mixed with a colloidal gold preparation 13A (FIG. 1B) containing a predetermined amount of gold particles 14A having antibodies 15A fixed to the outer surfaces thereof. Antibodies 15A specifically bind to antigen 12A (FIG. 1C). In the resulting mixture 16A, antigen 12A binds with available antibodies 15A, resulting in free complexes 18A, comprising both antigen 12A and antibody 15A bound to particles 14A. Since there are more antibodies 15A than antigens 12A, some antibodies 15A remain free, i.e., unbound to an antigen 12A.

As illustrated in FIGS. 2A-2C, the foregoing procedure is also carried out using a control sample 11B (FIG. 2) lacking the antigen 12A and a second colloidal gold preparation 13B (FIG. 2B) substantially identical in composition to preparation 13A used with patient sample 11A. The thus-formed second mixture 16B (FIG. 2C) lacks the complexes 18A shown in FIG. 1A, and correspondingly has a greater number of particles 14B having unbound antigen 15B on the surfaces thereof. The first mixture 16A, corresponding to the patient sample (FIG. 1C), and the second mixture 16B (FIG. 2C), corresponding to the control, are then ready for use with a corresponding reaction detector 20A, 20B according to the invention (FIGS. 1D, 2D).

Referring now to FIG. 3, reaction detector 20 includes a non-electrically conductive base 22, a pair of thin, spaced-apart electrically conductive layers 23, 24 disposed side-by-side on base 22 with a channel 32 formed therebetween, and means defining an electrical circuit, such as an ohmmeter 26 functionally connected to layers 23, 24 as shown by means such as wires 28. Layers 23, 24 act as a pair of positive and negative terminals for the circuit.

Referring again to FIGS. 1 and 2, identical first and second reaction detectors 20A (FIG. 1D) and 20B (FIG. 2D) are prepared in advance for use with mixtures 16A, 16B, respectively Samples of antigen in a carrier liquid (e.g., water or saline solution) are poured into shallow channels or grooves 32A, 32B defined between layers 23A,B and 24A,B to cause antigen to bind to the surfaces of bottom walls 33A,B of channels 32A,B to form antigen layers 30A, 30B (FIGS. 1D, 2D). These antigen layers 30A, 30B are made of the same type of antigen as antigen 12A to be detected.

Referring now to FIG. 1E, first mixture 16A (FIG. 1C), corresponding to patient sample 11A (FIG. 1A), is poured into channel 32A of first detector 20A to cause binding of antigen layer 30A and antibody 15A. The foregoing procedure is also carried out using the control mixture 16B (lacking complexes 18A) and second detector 20B (FIG. 2E). Conductive particles 14A having free antibodies 15A thereon effectively become bound to bottom wall 33A via antigen layer 30A due to the antigen-antibody binding reaction. Complexes 18A containing antigen 12A from sample 11A do not tend to become bound to bottom wall 33A.

After a suitable time to allow the antigen-antibody interaction to take place, channel 32A is flushed with a suitable liquid, e.g., water or saline solution, to wash away any unbound particles 14A, then dried by any suitable means, such as heating or allowing the reaction detector to stand open to the air. The resistance measurement can also be performed wet, without any drying step. Even when wet, the difference in measured resistance is sufficient to indicate whether the binding reaction has occurred.

Non-specific binding of particles to layers 30A, 30B occurs to some extent. Ordinary washing procedures may not be sufficient to remove such non-specifically bound particles from the antigen layer However, it has been found that ultrasonic treatment of the samples at a low level can remove non-specifically bound particles without removing specifically bound particles, i.e., particles bound due to antigen-antibody binding involving the substance being detected for. This is particularly important as a means of preventing a false positive result. Such a false positive result is a decrease in resistance due to non-specifically bound particles, rather than specifically bound particles.

Figure 4B:
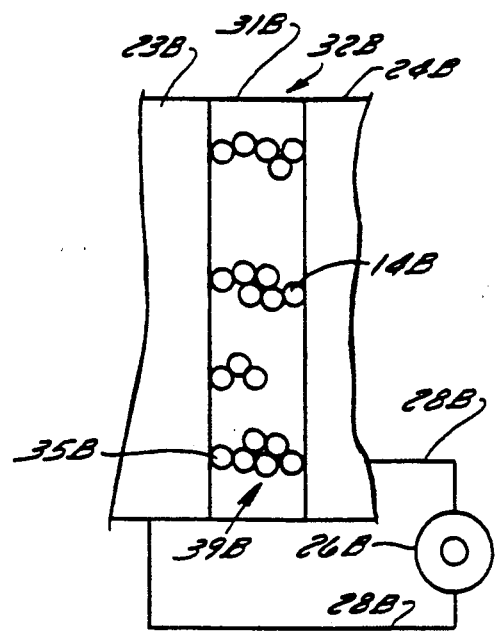

Referring now to FIGS. 4A and 4B, FIG. 4A corresponds to the same state as FIG. 1E, and FIG. 4B corresponds to the same state as FIG. 2E. FIGS. 4A, 4B illustrate the differences in the extent of the binding reaction not apparent in FIGS. 1E, 2E. Ohmmeters 26A and 26B register the resistance across channels 32A and 32B for each of the detectors 20A and 20B. For the control (FIG. 4B), all particles 14B having free antibodies 15B deposited thereon are available for binding with antigen layer 30B bound to bottom wall 33B. As a result, complexes 35B are formed at bottom wall 33B and are anchored thereto. As illustrated in FIG. 4B, complexes 35B tend to cluster together in contact with each other to form aggregates or chains 39B which effectively bridge channel 32B. Since particles 14B are electrically conductive, aggregates 39B effectively provide an electrical connection between layers 23B and 24B, completing an electrical circuit defined by ohmmeter 26B, wires 28B, layers 23B, 24B, and aggregates 39B. This is reflected by the resistance reading given by ohmmeter 26B. A drastic decrease in resistance occurs as a result of bridging of aggregates 39B.

The reaction for the mixture 16A corresponding to the patient sample proceeds in a similar fashion, except that this mixture 16A already contains complexes 18A formed by reaction of antigen 12A with antibody 15A. Since the antibodies of these complexes 18A are already bound with at least some antigen 12A, these complexes 18A do not tend to bind to the layer of antigen 30A at bottom wall 33A. In mixture 16A, the number of free antibodies 15A deposited on particles 14A is less than in mixture 16B, since some of these antibodies 15A were used to form complexes 18A. As shown in FIG. 4A, aggregates 39A form, but there are fewer such aggregates, and correspondingly less bridging of channel 32A. As a result, the decrease in resistance registered by ohmmeter 26A, if any, is less than the decrease in resistance registered by ohmmeter 26B. This difference in readings indicates the presence of antigen 12A in the patient sample 11A. If patient sample 11A does not contain any antigen 12A, then the decrease in resistance for reaction detector 20A would be the same as the decrease in resistance for detector 20B.

If resistance values corresponding to specific antigen levels in the sample are well known for a specific test, the foregoing procedure can be carried out without the control illustrated in FIGS. 2A-2E, 4B. However, the use of a control is preferred because the comparative resistance readings produced by the control afford more accurate results.

Figure 5:
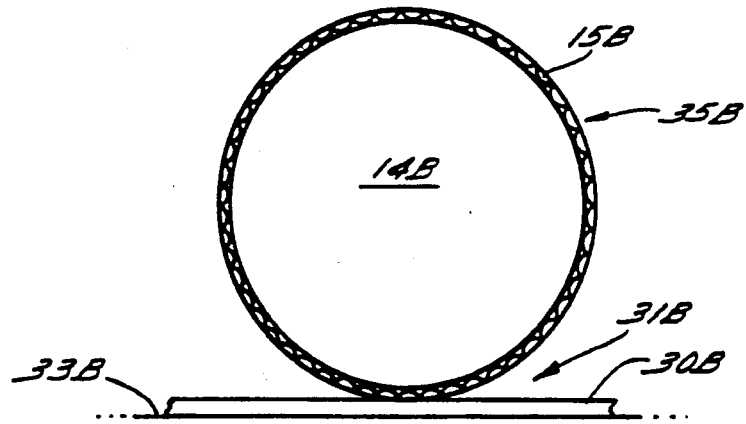
FIG. 5 is a schematic diagram showing binding of a conductive particle to a non-conductive base according to one embodiment of the invention.

The procedure shown in FIGS. 1 through 4 is greatly simplified for purposes of illustration. Conductive particles 14A,B are larger than antigen 12A and antibodies 15A,B. A number of antibodies 15A,B are bound to a single conductive particle 14A or 14B, and similarly a number of antigens 12A can bind with antibodies 15A on the surface of a single particle 14A or 14B. FIG. 5 schematically illustrates how a conductive particle 14B having antibodies 15B on its surface becomes bound to bottom wall 33B via antigen layer 30B.

The method of FIGS. 1-4 utilizes a positive control, that is, a decrease in resistance due to bridging of the channel by the conductive particles occurs for the control sample, not the unknown (patient) sample The method of the invention may also be carried out using a negative control wherein the sample containing the unknown, for example, an antibody, is reacted directly with the gold particles, and then the gold particles are brought in contact with the reaction surface coated with the corresponding antigen. The procedure is substantially the same as shown in FIG. 2B, except that the amount of the antibody is unknown.

Many variations of the method of the invention, including both competitive and non-competitive procedures, are possible. The process illustrated in FIGS. 1A-1E is a competitive reaction wherein the antigen is bound to the diagnostic element, and free antigen in the sample 11A competes with the bound antigen for sites on the conductively labelled antibody. The preincubation step shown in FIG. 1C may be omitted, and the sample 11A and colloidal gold 13A may be added directly to antigen layer 30A bound to the diagnostic element. Alternatively, the antibody may instead be bound to the diagnostic element, and conductively labelled antigen can compete with free antigen in the sample for antibody binding sites. In either case, the resistance measurements are directly related to the amount of free antigen in the sample, in other words, the measured resistance increases directly with increasing amounts of free antigen in the sample.

In a non-competitive variation useful for antigens that can bind to more than one antibody at the same time, a first antibody is bound to the diagnostic element in a predetermined amount in excess of the amount required to bind all available free antigen in the sample. The sample is added to the bound antibody and allowed to react. A second, conductively labelled antibody is added, either later or at the same time as the sample. The second antibody also reacts with the antigen, resulting in a complex comprising first antibody-antigen-second antibody-conductive particle bound to the diagnostic element. The two binding sites on the antigen may be identical, structurally different, or two-site immunometric. The resulting resistance measurements are inversely related to the amounts of free antigen in the sample, such that the resistance decreases as the amount of free antigen increases.

Another non-competitive variation is useful for determining amounts of specific antibody in a sample, particularly an antibody titer for a disease or allergy. The antigen is bound to the diagnostic element in sufficient excess to bind to the antibody in proportion to its concentration. A sample containing free antibody is added to the bound antigen and allowed to react. A secondary antibody carrying the conductive particles is added, either later or at the same time as the sample. The secondary antibody reacts with the first antibody, i.e., treats it as an antigen, forming a complex comprising antigen-first antibody-second antibody-conductive particle. The secondary antibody could be, for example, anti-immunoglobulin G or E. The resulting resistance measurements are inversely related to the amount of free (first) antibody in the sample. A secondary antibody can also be used in embodiments wherein resistance change is directly related to measured antigen in the sample in order to increase sensitivity.

Bases 22A, 22B discussed above must have a highly bioreactive surface "Bioreactive" as discussed herein refers to the ability of the surface to bind biogenic substances such as proteins or nucleotides. Bioreactivity values measured for various organic and inorganic substances vary widely even among chemically similar substances. However, certain plastics and metal oxides and nitrides are generally bioreactive. In a series of enzyme immunoassay experiments (see Example 3) the absorption of light at 490 nanometers was used as a standard for determining binding by a rabbit IgG-goat anti-rabbit IgG complex to each surface tested. Nylon 66 had the highest level of bioreactivity measured. For purposes of the present invention, substances having a bioreactivity at least 70% that of Nylon 66 for proteins are considered highly bioreactive. Compounds having about 50–70% as much bioreactivity as Nylon 66 are mildly bioreactive, compounds having 10–50% are somewhat bioreactive, and compositions having a bioreactivity of about 10% or less are bioinert.

It has been found that the following substances are highly bioreactive with proteins: Nylon 66, polypropylene, mylar, chromium oxide, phenolic plastic, polystyrene, and vinyl. Chromium oxide is unusually high in protein bioreactivity for a metal oxide. Moderately bioreactive substances for proteins include chromium, titanium oxynitride, nickel oxide, tantalum nitride and carbon. Poorly bioreactive substances for proteins include titanium oxide, boron nitride, and silicon oxide. Bioinert substances for proteins include silicon nitride, barium titanium oxide, indium tin oxide, aluminum oxide and glass.

Figure 6:
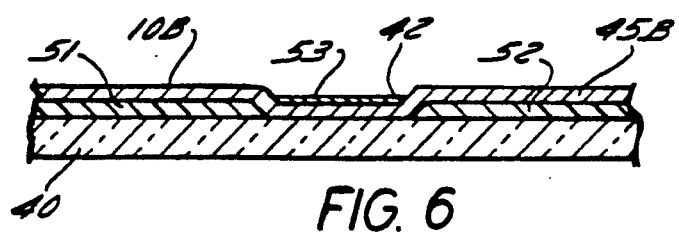
FIG. 6 is a cross-sectional view of a diagnostic element according to one embodiment of the invention.
Figure 7:
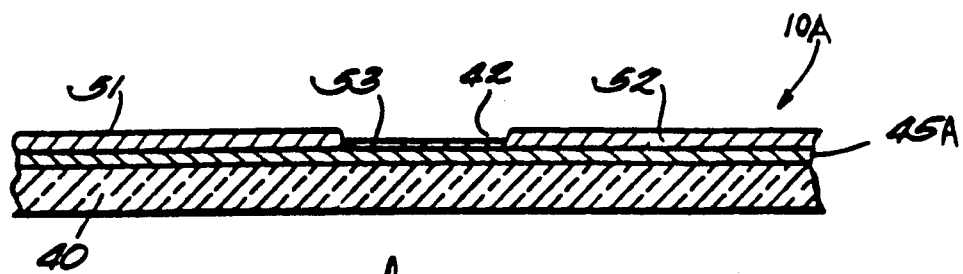
FIG. 7 is a cross-sectional view of an alternative diagnostic element according to the invention.

FIGS. 6 and 7 illustrate two diagnostic elements 10A, 10B that can be used in the method of the invention. In FIG. 7, diagnostic element 10A according to the invention includes a support 40 such as a glass plate, e.g. a microscope slide, coated with a thin layer 45A of an electrically resistive, bioreactive substance such as chromium oxide. A pair of conductive layers, such as chromium metal layers 51, 52, are superposed on the resistive, bioreactive layer 45A. A channel 42 separates layers 51, 52. A layer of an antigen 53 spans channel 42, and may also cover layers 51, 52. Layers 45A, 51, 52 are preferably formed by sputtering on a glass plate. Channel 42 is then formed by photolithography using an etchant that selectively attacks the conductive layer but does not attack layer 45A. In this diagnostic element, the width of channel 42 relative to the size of the conductive particles to be used is important because the binding reaction is primarily indicated by complete bridging of channel 42 by aggregates of the conductive particles. The resistive layer 45A is highly resistive, i.e. more than about $10^6$ ohms-cm, so that virtually no change in resistance is caused by partial bridging as shown in FIG. 4A.

FIG. 6 illustrates an alternative diagnostic element wherein conductive layers 51, 52 are formed directly on support 40, with channel 42 formed therebetween. Resistive layer 45B is superposed over support 40 and layers 51, 52, and antigen layer 53 is then formed thereon. In this embodiment layer 45B is only moderately resistive, e.g. $10^3$–$10^6$ ohms-cm, so that a substantial change in resistance will occur due to resistive shunting of current through aggregates bound to layer 53, even when no complete bridging occurs.

FIG. 12 illustrates a resistor through which resistive shunting occurs. In seeking the path 71 of least resistance, the current will be shunted through bound aggregates 72 which offer a lower resistance than the support 40. The overall resistance drop across channel 42 will depend on how many aggregates are bound, and can provide a quantitative indication of the amount of binding being measured. In the resistor shown, the calculated resistance drops from 70,000 to 40,030 ohms following the reaction.

The width of channel 32 or 42 may vary, particularly in relation to the simple numerical average diameter of the conductive particles forming a chain to bridge the channel. The following table states preferred ranges for dimensions for gap-bridging embodiments according to the present invention:

TABLE 1

| Average Particle Diameter (Microns) | Channel Width (Microns) | Ratio of Channel Width to Particle Diameter |
|---|---|---|
| 0.01–500 | 0.1–20,000 | 5:1 to 40:1 |
| 0.01–10 | 0.1–100 | 10:1 to 30:1 |
| 0.01–1 | 1–25 | 15:1 to 25:1 |

A 20:1 ratio of channel width to average particle diameter is typical, e.g., the channel has a width of 10 microns, and the average diameter of the conductive particles is 0.5 microns. The foregoing ranges are also useful in resistive shunting embodiments, but much larger channel widths may be employed, such as up to 1 mm, 1 cm, or greater, depending on the desired application.

As an alternative to a channel, diagnostic elements according to the invention, especially resistive shunting embodiments, may utilize a resistive, bioreactive path other than a channel. Such a path may comprise, for example, a curved line which spans the conductors but does not represent the shortest distance between them. Similarly, the conductors need not be in the form of layers. Small wires superposed on the base can, for example, be employed as the conductors.

Proteins have an affinity for materials such as polystyrene, chromium oxide and the like, and tend to become bound thereto under suitable conditions. Proteins can also readily become bound to the surfaces of fine metal particles, such as gold particles, using the procedure described below. In embodiments of the invention which involve antigen-antibody binding, it is preferred to bind the antigen to the bottom wall of the channel and bind the antibodies to the conductive particles. However, the reverse arrangement (antigen-particles, antibody-channel) can also be employed.

Conductive layers 51, 52 may have any desired dimensions which prove functional. To reduce the size of the diagnostic element, these layers are generally as thin as possible, and preferably have a thickness no greater than about 5 microns, preferably no greater than about 0.5 microns, particularly a thickness in the range of 0.001–0.005 microns. Conventional sputter deposition can be readily used to form the conductive layers in any desired shape.

Layers 51, 52 (or 23, 24) may be formed of any suitable conductive material, particularly an electrically conductive metal such as gold, silver, platinum, copper, chromium or aluminum. Particles 14A, 14B are preferably made from a conductive metal such as gold, silver, or platinum, and may also be made of carbon platelets or plastic particles having a conductive metal coating, especially gold-coated polystyrene spheres. Such coated spheres are lighter than comparable solid metal spheres and are thus better able to maintain bonding to the surface.

The extent of binding of an antibody to metal particles is influenced by various factors. A series of enzyme immunoassay experiments demonstrated that affinity-purified antibody tends to bind to gold particles to a much greater extent than impure, whole serum antibody, and that the pH of the system also had a strong effect. A slightly acidic pH (e.g. 6–7) produced severalfold greater binding than a basic pH of 9–10 for large (greater than 0.5 $\mu$m diameter) particles. Polyethylene glycol treatment of the gold particles may also be used if needed to stabilize large gold particles; see Horisberger et al., *J. Histochem. Cytochem.*, 25:295–305 (1977).

The antibody concentration on the gold particles should be high enough to allow the antigen-antibody reaction to occur on the surfaces of the gold particles to an extent sufficient for detection by the method of the invention. On the other hand, if the antibody concentration is too great, the antibody layer may have an insulating effect which will result in a false negative result, i.e., will block the drop in resistance that would normally occur, unless an additional step of overcoating the aggregates with a conductive metal is used, as described hereafter.

Base 22 described above is made of a bioreactive plastic, preferably polypropylene, mylar, phenolic plastic, vinyl, methyl cellulose, nylon or polystyrene. The polarity of protein molecules causes such molecules to bind to such a plastic base to form a substantially complete, homogenous coating of antigen. Glass by itself is not generally employed as the base (support) since antigens have a poor affinity for a glass surface and it has proved difficult to adhere a layer of antigen to a glass slide. However, according to a further aspect of the invention, it has been found that a glass slide can be surface treated so that antigen affinity for the coating on the glass slide becomes as great or greater than antigen affinity for a conventional polystyrene slide. As noted above, this surface treatment comprises coating the glass support 40 with a thin layer 45A or 45B of a material having a moderate to high electrical resistance as compared to the conductive layers. The resistance of this layer is in the range $10^3$–$10^8$ ohms-cm, preferably $10^4$–$10^7$ ohms-cm, as compared to a resistance of less than 100 ohms-cm for the conductors. Moderately resistive materials for purposes of the invention are those having measured resistances in the range of $10^3$ up to $10^6$ ohms-cm when deposited on a glass support, whereas highly resistive materials have comparable measured resistances of $10^6$ or more.

Bioreactive substances suitable for forming layer 45A or 45B include carbon, hydrophilic organic polymers, and inorganic metal oxides and nitrides. Such inorganic metal compounds include oxides, nitrides and oxynitrides of boron, aluminum, silicon, cadmium, copper, nickel, cobalt, iron, manganese, and metals of Groups IIA, IIIB through VIB. Especially preferred inorganic metal compounds include chromium oxide ($CrO_3$), titanium oxynitride ($TiO_xN_y$), tantalum nitride, cermet materials such as chromium/silicon oxide (Cr.SiO) or gold/silicon oxide, and other inorganic materials currently used in resistors. Hydrophilic organic polymers include well-known plastics such as mylar, polystyrene and nylons, such as Nylon 66.

If chromium oxide is used as layer 45A, it is usually deposited in the form of $CrO_2$. To make it more bioreactive, the layer may be aged in the presence of oxygen and water vapor to convert it to $CrO_3$, which is hydrophilic. This aging can be accelerated by placing the coated base or finished diagnostic element in a humidity chamber. Carbon in any convenient form, e.g. graphite, is a theoretically ideal material for layer 45 in view of its biocompatability, although its thin film resistance may be hard to control within narrow ranges.

Cermet resistor materials have a high resistance, are stable, and have low negative temperature coefficients, such that the diagnostic element will not be excessively temperature sensitive When heated in air, cermet films oxidize and increase in resistance, and are usually provided with a protective overcoating to prevent oxidation and/or hydration. In the present invention, however, layer 45 does not require such a protective coating.

Figure 8:
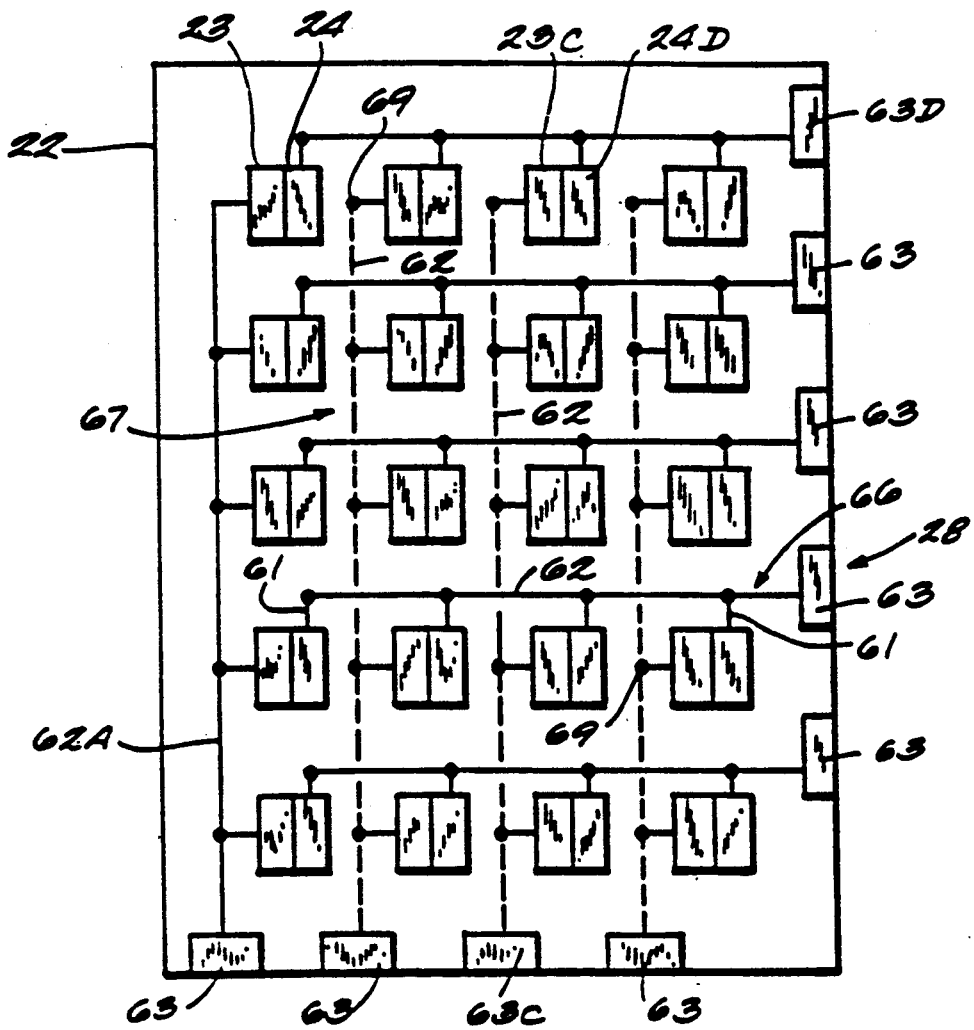
FIG. 8 is a plan view of a multiple diagnostic element according to the invention.

FIG. 8 illustrates a further embodiment of the diagnostic element of the invention wherein a multiplicity of reaction sites are disposed on a single non-conductive base 22. Each reaction site comprises a pair of conductors, such as layers 23, 24, having a layer of a biogenic substance which undergoes specific binding disposed in the channel or path therebetween. The biogenic substance, such as an antigen, may be the same or different for each reaction site. Conductive means 28 for this embodiment comprises a series of individual electrical conductors 61 which each connect to a common conductor 62, which in turn connects to a terminal plate 63 mounted on the edge of base 22. Pairs of layers 23, 24 are arrayed in rows and columns on base 22.

In the embodiment of FIG. 8, rows of plates 63 are disposed on adjacent sides of rectangular base 22. To prevent overlapping between a first set 66 of conductors 62 connected to layers 23 and a second set 67 of conductors 62 connected to layers 24, all but one of conductors 62 of second set 67 are located on the reverse side of base 22. These conductors 62 are illustrated by broken lines in FIG. 8. Outer conductor 62A does not cross any conductors 62 of first set 66 and thus does not need to be on the other side of base 22, although it can be so located if desired. Individual conductors 61 connected to common conductors 62 of second set 67 on the reverse side of base 22 include portions 69 which extend through the thickness of base 22 and connect with such conductors 62, shown by broken lines in FIG. 8.

Ohmmeter 26 can be connected to various combinations of terminal plates 63 to measure resistance for each pair of layers 23, 24. To make such a measurement, ohmmeter 26 is connected to two plates 63 on different edges of base 22. Connecting an ohmmeter to plates 63C, 63D would test the indicated pair of layers 23C, 24D. This embodiment allows a single diagnostic element according to the invention to test a single patient sample for a number of different substances, such as antigens, since each pair of layers 23, 24 can have a different substance bound therebetween, or have no substance bound therebetween so as to provide a control. In the alternative, the same substance may be tested for a number of times to provide a more certain result.

In an alternative embodiment shown in FIG. 9, terminals 63 are disposed along only one edge of base 22. One terminal 63E is connected to each layer 23 by a single, multibranched conductor 62E. A series of terminals 63F are each connected to one of layers 24 by separate conductors 62F. Conductors 62E,F are arranged to not cross each other, so that all of conductors 62E,F are disposed on the front face of the diagnostic element as shown. For this purpose terminal 63E is located at one end of the row of spaced-apart terminals 63E,F. This embodiment avoids the need to provide wires, conductive lines, or the like on both sides of the plate, and allows the terminals to be disposed on a common edge.

Resistive shunting according to the method of the invention may be greatly enhanced by overcoating the aggregates with a layer of a conductive substance, particularly a metal such as silver, gold, or platinum. The applied coating must stick selectively to the aggregates but not to the remainder of the the path between the conductors. If gold particles are used as the particles to which one of the binding substances are bound, silver enhancement may be used to form a conductive silver coating over the aggregates.

Conductive metal overcoating is especially useful for resistive shunting embodiments of the invention for two reasons. First, it can eliminate problems with junction resistance effects. Referring to FIG. 10, resistive shunting is minimized by the relatively small contact surface of the aggregates 76 with the underlying layer 53. In addition, the biogenic coating 77 on the gold particles 78 can form an insulating barrier such that the junction resistance $R_j$ is high enough to prevent resistive shunting. By contrast, the conductive metal coating 79 shown in FIG. 11 creates a much lower resistance $R_j$ and allows resistive shunting to occur. This embodiment of the invention is especially preferred because it improves reliability, as demonstrated by the results of Example 2 below.

Second, metal overcoating can eliminate the need to use particles which are both bioreactive and conductive. Since the metal overcoating can conduct the current, the particles can be made of a non-conductive substance, e.g., non-conductive beads may be used so long as the metal overcoating sticks selectively thereto. This advantage also pertains to gap bridging embodiments as well.

The following examples describe a gap bridging embodiment (Example 1), a resistive shunting embodiment (Example 2) and an example of a procedure for determining bioreactivity according to the invention (Example 3).

EXAMPLE 1

A. Preparation of Colloidal Gold

The following procedure was used to make a suspension of gold particles. Glassware including a flask and stirring bar were cleaned by sonication in a bath sonicator, first in ethanol, then acetone, then petroleum ether, for about 5 minutes each. The glassware was then blown dry with a Freon refrigerant, then rinsed twice with double glass-distilled water. About 1 ml (milliliter) of a 1% w/v (weight/volume) filtered solution of gold chloride in water and 99 ml of filtered, double glass distilled water were added to the cleaned flask. The resulting mixture was then heated and stirred with the cleaned stirring bar until boiling. At that time 300 $\mu$l of a 1% w/v filtered solution of trisodium citrate in water was added. Boiling was continued with stirring, and additional 1% trisodium citrate solution was added in amounts of 100, 50 and 50 $\mu$l at intervals of 5, 12 and 15 minutes, respectively, from the time the mixture began boiling. After 30 minutes of boiling the flask was removed from heat and allowed to cool. The average particle size of the resulting colloidal gold particles was 100 nm as determined using a transmission electron microscope. The flask containing the colloidal gold preparation was sealed and stored at 4° C.

B. Preparation of Gold-Labelled Proteins

About 9 ml of the colloidal gold preparation made in part A above, 100 $\mu$l of 0.2 M potassium carbonate and 20 $\mu$l of a protein, an affinity-purified goat anti-rabbit immunoglobulin (IgG) antibody, were added to a 15 ml conical centrifuge tube. The ingredients were mixed overnight on a tube rotator. 1 ml of a filtered aqueous polyethylene glycol solution (2 mg PEG/ml) was then added as a stabilizing agent. Filtration in this and subsequent procedures was carried out using a 0.2 micron filter disk fitted into a syringe. The resulting gold-protein conjugates were concentrated by centrifugation at 11,000 rpm for 10 minutes. The supernatant was discarded, and the resulting pellet of gold particles was pipetted into a 1.5 ml centrifuge tube. The particles were then washed by centrifugation four times with a phosphate buffered saline solution (0.01 M sodium phosphate dibasic, 0.15 M sodium chloride, 0.1 mg/ml polyethylene glycol, pH 7.4) containing 0.2% sodium azide as a preservative to remove unbound protein. The conjugated gold particles were then resuspended in 1.4 ml of phosphate buffered saline solution containing 0.2% sodium azide.

C. Preparation of Diagnostic Element

A glass slide was coated with a thin layer of chromium oxide ($CrO_x$, wherein $x = 1-3$) by radiofrequency (rf) magnetron sputter deposition using a Materials Research Corporation Model 822 Sputtersphere. A chromium plate target was used as the cathode. The glass slide was placed on a copper plate anode disposed beneath the cathode. Deposition was carried out under the following conditions: system base pressure $3 \times 10^{-7}$ Torr, total pressure $8 \times 10^{-3}$ Torr, forward power 1,000 W, target voltage 335V, reflected power 0 watts, cathode to anode distance 2½ inches, and a sputtering time of 30 minutes. The system was backfilled with oxygen. The desired chromium oxide layer having a thickness of about 0.1 $\mu$m was thereby formed by deposition in the oxygen plasma A layer of chromium was then deposited over the chromium oxide layer by repeating the foregoing procedure in an inert argon plasma, resulting in a surface layer of chromium having a thickness of 1 μm.

D. Photolithography

A line having a width of 5 μm was then formed in the surface chromium layer of the double-coated slide of part C by photolithography. In yellow room light, a layer of photoresist plastic was first formed over the chromium layer as follows. The twice-coated slide was placed in the chuck of a Headway Model EC101 spinner under vacuum. About 3 ml of Shipley 111S photoresist was applied over the chromium layer and allowed to spread for 10 seconds. The slide was then spun at 2000 rpm for 30 seconds to form a uniform 1 μm thick photoresist coating. Several such photoresist-coated slides were then baked in a hot plate oven on a rack for about 20 minutes at 80° C., then allowed to cool for 5 minutes.

A Suss MJB55 photolithographic mask aligner was calibrated and prepared for use. A mask defining a 5 μm line was cleaned thoroughly with dissolved soap and water, then dried with a nitrogen stream that left no residue. The mask was then placed in a mask holder under vacuum, and the mask holder was then placed in position on the aligner. The triple-coated slide was placed beneath the 5 μm line of the mask. The mask holder was then locked in place, and the aligner was used to expose the photoresist layer to UV light for 18 seconds. The exposed slide was then removed from the aligner.

The slides were then immersed in a fresh 4:1 developer solution (4 parts water to 1 part Shipley 303A developer) for 2 minutes with no agitation, and then promptly rinsed with distilled water. Each slide was then immersed in the etchant, a solution heated to 45° C. consisting of 90.8 g $AlCl_3$, 27.0 g $ZnCl_2$, 6 ml $H_3PO_4$ and 80 ml distilled water, for about 10 seconds. During this time the etchant removed undeveloped photoresist material and chromium metal along the 5 micron line which was previously exposed to UV light. However, the etchant did not attack the chromium oxide layer. After etching, the slide was promptly rinsed in distilled water. The photoresist material was then removed from the surface of the chromium layers by immersing the slides for about 5 minutes in Shipley 1112A remover. Thereafter the slide was rinsed thoroughly in tap water, then rinsed ultrasonically in distilled water for 10 minutes. The slide was then re-immersed in the remover, and the rinsing steps were repeated to ensure that the photoresist material was completely removed.

E. Measurement of Binding Reaction

The resistance of the diagnostic elements prepared in part D was measured using an ohmmeter. Each element was then placed in a test tube and rinsed with a coating buffer (0.015 M sodium carbonate, 0.035 M sodium bicarbonate, 0.003 M sodium azide, pH 9.8). Pairs of diagnostic elements were prepared by adding either rabbit immunoglobulin (IgG) or bovine serum albumin (BSA) to each test tube. The elements were incubated by allowing the tubes to stand overnight at room temperature. The protein-coated elements were then washed three times with a PBS-Triton buffer (phosphate buffered saline solution as described above containing 0.1 vol. % Triton X-100 as a wetting agent) to remove excess unbound protein. The coated substrates were then placed on a piece of parafilm in a petri dish. The colloidal gold-protein conjugate was then applied to each element in an amount sufficient to cover the upper surface of each element, and the elements were allowed to incubate (stand) for 20 minutes at room temperature. Each element was then washed by aspiration once in PBS-Triton buffer and once in distilled water, and then allowed to air dry for 1 hour. The resistance of each element was then measured using the same ohmmeter as initially used to measure the resistance of each element.

All elements tested had a starting resistance greater than 2 million ohms. Positive results were obtained for samples at line widths of 3, 5, 6 and 7.5 μm. For these samples, the measured resistance at the second measurement, following the reaction, dropped to values ranging from 85 to 700 ohms. A few IgG samples resulted in weakly positive results ranging from 80,000 to 800,000 ohms. Negative results were obtained for the BSA samples (the resistance after the reaction remained higher than 2 million ohms), except that two weakly positive results for BSA samples were obtained at the 5 μm line size.

Similar results were obtained when the foregoing procedure was repeated at different temperatures or incubation times. Usually, a positive result was obtained with a reaction time of 20 minutes. These variations of the procedure indicate that the reaction time can be shortened substantially.

EXAMPLE 2

A. Preparation of protein-labelled colloidal gold and diagnostic elements

Protein labelled colloidal gold was prepared as described in Example 1, parts A and B. A diagnostic element according to the invention was then prepared by first coating a glass microscope slide with a thin layer of chromium by rf magnetron sputter deposition using the procedure of Example 1, part C, except that no intervening layer of chromium oxide was formed. The chromium-coated slide was then subjected to photolithography as described in Example 1, part D, except that the line formed had a width of 1 millimeter.

A thin layer of carbon was then deposited over the entire upper surface of the slide, as shown in FIG. 6, by sputter deposition according to Example 1, part C, except as follows: the backfill gas was argon, and the target (cathode) was a a graphite disk 8 inches in diameter and 0.25 inch thick. The graphite disk was epoxyed to a water-cooled copper backing plate. Deposition was carried out at 145 V with a forward power of 200 W. The desired carbon layer having a thickness of about 0.25 μm was thereby formed by deposition in the argon plasma.

B. Measurement of Immunologic Reaction

The resistance of the diagnostic elements prepared in part A was measured using an ohmmeter. Each element was then placed in a test tube and rinsed with a coating buffer (pH 9.8, as described above). Pairs of positive and negative diagnostic elements were prepared by adding either rabbit immunoglobulin (IgG) or bovine serum albumin (BSA) to each test tube. The elements were incubated by allowing the tubes to stand overnight at room temperature. The protein-coated elements were then washed three times with a PBS-Triton buffer (phosphate buffered saline solution as described above containing 0.1 vol. % Triton X-100 as a wetting agent)

to remove excess unbound protein. The coated substrates were then placed on a piece of parafilm in a petri dish. The colloidal gold-protein conjugate was then applied to each element in an amount sufficient to cover the upper surface of each element, and the elements were allowed to incubate (stand) for 2, 1 or ½ hour at room temperature. Each element was then washed once in PBS-Triton buffer and once in distilled water, and then allowed to air dry for 1 hour. The resistance of each element was then measured using the same ohmmeter as initially used to measure the resistance of each element.

C. Silver Enhancement

The elements prepared in part B above were rewashed with distilled water to remove chloride ions that might react with the silver enhancement reagents. A 2 M sodium citrate buffer solution, a 0.5 M hydroquinone solution and a 0.03 M silver lactate solution were prepared in a darkened room. The three reagents were then mixed together to provide 25 ml of overcoating reagent. The elements were completely immersed in this reagent for 2-3 minutes, then immersed in a 1% acetic acid solution for 2 minutes, and then immersed in a fixative solution for for 2 minutes The fixative used was Kodak Rapid Fix, containing ammonium thiosulfate, acetic acid, sodium metabisulfite, sodium tetraborate, and aluminum sulfate. The elements were rinsed in distilled water for 10-15 minutes and allowed to air dry. The resistance of each element was then measured using the same ohmmeter as used in Example 2, part B.

The resistance results (R) are summarized in Table 2. In part B, Samples 6A, 6B were incubated for 1 hour, Samples 7A, 7B were incubated for ½ hour, and the remaining samples were incubated for 2 hours.

TABLE 2

| Sample | Starting R (Ohms) | R After Gold (Ohms) | R After Silver Enh. (Ohms) | % Change |
|---|---|---|---|---|
| 1A (BSA) | 298,000 | 394,000 | 304,000 | +0.002 |
| 1B (IgG) | 357,000 | 444,000 | 379 | −99.9 |
| 2A (BSA) | 1,060,000 | 1,280,000 | 950,000 | −10.0 |
| 2B (IgG) | 1,110,000 | 1,270,000 | 6,800 | −99.1 |
| 3A (BSA) | 4,900,000 | 6,210,000 | 4,050,000 | −17.3 |
| 3B (IgG) | 5,460,000 | 6,560,000 | 1,410,000 | −74.2 |
| 4A (BSA) | 39,800 | 71,500 | 43,500 | +9.3 |
| 4B (IgG) | 38,800 | 59,300 | 192 | −99.5 |
| 5A (BSA) | 3,600,000 | 3,600,000 | 2,600,000 | −27.8 |
| 5B (IGG) | 1,100,000 | 1,100,000 | 603 | −99.9 |
| 6A (BSA) | 48,600 | 85,200 | 71,000 | +46.1 |
| 6B (IGG) | 72,500 | 130,300 | 920 | −98.7 |
| 7A (BSA) | 29,400 | 50,300 | 41,400 | +40.8 |
| 7B (IGG) | 42,600 | 69,400 | 690 | −98.4 |

An increase in resistance of about 10-100% normally occurs when the carbon films of Example 2 are exposed to water. At a channel width of 1 mm, no complete bridging occurs which might cause a decrease in resistance. However, resistive shunting embodiments according to the invention can successfully detect a binding reaction even without metal overcoating if a narrow channel width (or shorter path) is used, and other reaction conditions are adjusted accordingly.

D. Ultrasound Procedure

A pair of BSA and IgG diagnostic elements were prepared according to the procedure of Example 2, part B, using a 2 hour incubation period. After 2 hours both surfaces were washed and dried. A high level of gold particle binding was observed microscopically for the IgG sample, and a moderate to low amount of binding was observed for the BSA sample. Both samples were then immersed in distilled water and subjected to 1 minute of treatment with a Virsonic 50 Virtis cell disrupter at its lowest power setting. The samples were then removed and reexamined. No difference in the amount of gold binding was observed for the IgG sample, whereas most of the previously observed gold particles on the BSA sample were removed by the treatment. In another experiment in which a similar ultrasonic treatment was used, a false positive sample (a BSA sample for which a drop in resistance was noted) of the type described in Example 1, part E, was converted to a negative sample.

EXAMPLE 3

The bioreactivity of various substances was measured by the following procedure. The surface to be tested was cut to a size of 1 square cm. For metal oxides and nitrides, the procedure of Example 1, part C, was varied as needed to prepare thin film-coated glass test samples. The square samples were placed in test tubes. One ml of a coating buffer as described above was added to each tube to fully cover each surface. The tubes were shaken gently to wash the surfaces, and then the buffer was removed by aspiration. One ml of a solution of 5 μg/ml rabbit IgG in coating buffer was added to each tube. One ml of 1% BSA in coating buffer was added to each of a duplicate set of tubes as negative controls. All tubes were shaken gently, then allowed to incubate overnight at room temperature. The IgG proteins thereby became bound to the surfaces.

The coating solutions were then removed by aspiration and washed once with PBS-Triton solution (described above). The test samples were transferred to clean test tubes and washed twice more with PBS-Triton solution. One ml of goat anti-rabbit IgG antibody-peroxidase conjugate diluted 1:4000 parts by volume in a PBS-G solution (0.01 M sodium phosphate dibasic, 0.15 M sodium chloride, 0.1% gelatin) was added to each test tube. The tubes were allowed to incubate for 30 minutes, then the conjugate solution was removed by aspiration, and each sample was washed 3 times with PBS-Triton solution to remove excess unbound antibody. One ml of 2 mg/ml o-phenylenediamine (OPD) in a substrate buffer (0.058 M sodium phosphate dibasic, 0.023 M citric acid, pH 5.6) and containing 4% hydrogen peroxide was added to each tube. The OPD dye was activated by the antibody-peroxidase conjugate to produce a yellow color which absorbs light at 490 nm.

The tubes were incubated for 5 minutes at room temperature, then the reaction was stopped by adding 0.4 ml of 2 M sulfuric acid to each tube, and each tube was mixed. 300 μl of each tube was transferred to a well of a microtiter plate, and 300 μl of water was also placed in a well as a reference blank. Absorbance measurements for each well were made using a Bio-Tek Automated Microplate Reader Model EL309. The amount of protein bound to each sample is directly proportional to the absorbance of the corresponding sample in Absorbance Units (AU) at 490 nm. The results were:

TABLE 3

| Sample | Binding Ability (%) |
|---|---|
| Nylon 66 | 100 |
| Polypropylene | 90 |
| Mylar | 89 |
| Chromium oxide | 83 |

TABLE 3-continued

| Sample | Binding Ability (%) |
|---|---|
| Phenolic plastic | 78 |
| Polystyrene | 73 |
| Vinyl | 65 |
| Chromium | 59 |
| Nickel oxide | 52 |
| Styrene | 29 |
| Titanium oxide | 16 |
| Boron nitride | 13 |
| Silicon oxide | 10 |
| Silicon nitride | 7 |
| Barium titanium oxide | 6 |
| Indium tin oxide | 6 |
| Aluminum oxide | 6 |
| Glass | 4 |

For the BSA controls and the samples for IgG bioinert surfaces such as glass, the antibody-peroxidase conjugate did not bind, so that the OPD did not change color and the absorbance at 490 nm was low. Correspondingly higher absorption values were obtained by bioactive substances tested, such as chromium oxide and Nylon 66. Somewhat different results were obtained when the experiment was repeated using four DNA-coated surfaces instead of protein-coated surfaces. Chromium oxide showed the highest bioreactivity (0.531 AU), followed by glass (0.393 AU), titanium oxide (0.378 AU) and then polystyrene (0.279 AU). Metal oxides thus seem to have a better affinity for nucleotides than plastics such as polystyrene.

EXAMPLE 4

The sensitivity of the method of the invention was evaluated by determining a limiting amount of antibody required for an assay. Diagnostic elements were prepared by cutting conductive polyimide plastic (Kapton containing blended carbon) into 1 cm by 0.3 cm squares. The pieces were rinsed once in coating buffer (described above) and immersed overnight at room temperature in test tubes containing either 1% BSA in coating buffer or 5 $\mu$g/ml rabbit IgG (the antigen). The resulting sample elements were then washed three times with PBS-Triton solution (described above) and placed on parafilm in petri dishes. A solution of goat anti-rabbit IgG antibody bound to gold particles, prepared according to the procedure of Example 1, Parts A and B, was serially diluted, and two drops at each dilution were applied to one BSA-coated sample and one IgG-coated sample. After 2 hours of incubation at room temperature, the samples were first washed with PBS-Triton solution, and then with distilled water. The samples were then allowed to dry, and the resistance of each sample was measured. Silver overcoating was then carried out for each sample using the procedure of Example 2, part C. The resistance of each sample was then measured, and the number of silver counts at each dilution was determined by x-ray analysis.

The results were as follows, wherein resistance values (R) are given in megaohms except where noted:

TABLE 4

| Sample/ Dilution | | Starting R | R After Gold | R After Silver | Silver Counts |
|---|---|---|---|---|---|
| 1A (BSA) | None | 1.55 | 2.02 | 1.46 | — |
| 1B (IgG) | None | 1.48 | 1.72 | 112 ohms | 2861 |
| 2A (BSA) | 1:2 | 1.52 | 2.11 | 1.28 | — |
| 2B (IgG) | 1:2 | 1.47 | — | — | 2187 |
| 3A (BSA) | 1:4 | 1.52 | 1.94 | 1.67 | — |
| 3B (IgG) | 1:4 | 1.53 | 1.57 | 0.31 | 1723 |

TABLE 4-continued

| Sample/ Dilution | | Starting R | R After Gold | R After Silver | Silver Counts |
|---|---|---|---|---|---|
| 4A (BSA) | 1:8 | 1.41 | 1.60 | 1.43 | — |
| 4B (IgG) | 1:8 | 1.41 | 1.57 | 0.54 | 1174 |
| 5A (BSA) | 1:16 | 1.40 | 1.58 | 1.41 | — |
| 5B (IgG) | 1:16 | 1.49 | 1.57 | 0.62 | 748 |
| 6A (BSA) | 1:32 | 1.48 | 1.85 | 1.46 | — |
| 6B (IgG) | 1:32 | 1.47 | 1.82 | 1.06 | 699 |

Figure 13:
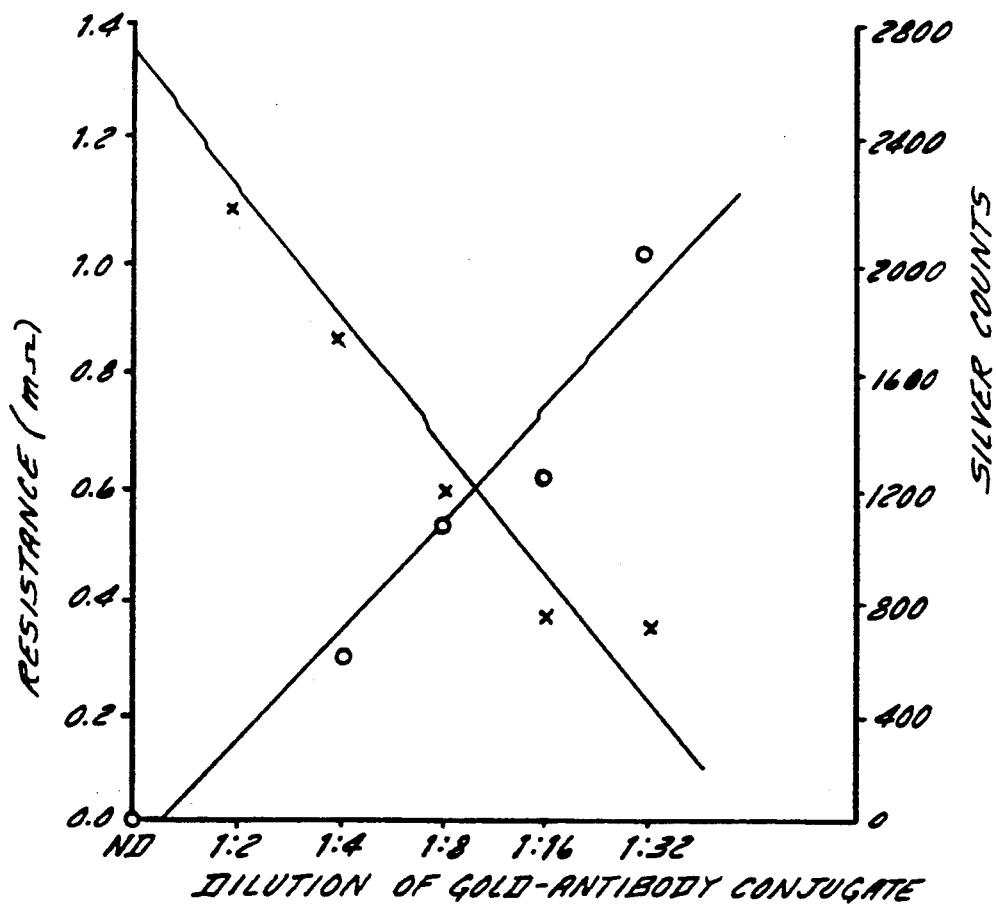
FIG. 13 is a graph wherein resistance values after silver overcoating and silver counts, both as obtained in Example 4, are plotted against gold-antibody conjugate dilution.

Resistance values after silver overcoating and silver counts obtained in this example are plotted against gold-antibody conjugate dilution in FIG. 13, wherein X's represent silver counts and circles represent resistance in megaohms. The limiting antibody concentration was found to occur at a dilution of about 1:8. The resistance and silver count values both varied substantially linearly with concentration, and the change in resistance was found to vary inversely with the number of silver counts, demonstrating that the extent of resistive shunting was directly related to the number of silver overcoated aggregates bound to the surface.

EXAMPLE 5

The sensitivity of the method of the invention was further evaluated by generating a dose response curve. Diagnostic elements were prepared by cutting conductive Kapton plastic as described in Example 4 into 2.3 cm by 0.3 cm pieces. Titanium metal contact pads (0.5 by 0.3 cm) were disposed at opposite ends of each strip 1.3 cm apart to form resistors. The resistance of each resistor was then measured. The resistors were rinsed once with coating buffer, incubated in rabbit IgG, and washed three times using the procedure of Example 4. Dilutions of rabbit IgG in coating buffer containing rabbit IgG in the amounts given in Table 5 below were prepared and preincubated with gold-goat anti-rabbit IgG conjugate prepared according to Example 4 at a 1:8 dilution for 11.5 minutes. The preincubated conjugate was then applied to the sample resistors disposed on parafilm in petri dishes and allowed to incubate for 2 hours at room temperature. The samples were then washed once with PBS-Triton solution and once with distilled water, and allowed to dry. The resistance of each sample was then measured by connecting an ohmmeter to each of the contact pads. The samples were then silver overcoated as described in Example 2, part C, and the resistance of the samples was again measured.

The results were as follows, wherein the resistance values (R) are expressed in kiloohms and the amount of rabbit IgG (antigen) is expressed in nanograms:

TABLE 5

| Sample | Rab.IgG Amount | Starting R | R After Gold | R After Silver | % Change |
|---|---|---|---|---|---|
| 1A | 1000 | 311 | 349 | 335 | −4.0 |
| 1B | 1000 | 318 | 355 | 340 | −4.2 |
| 2A | 500 | 391 | 410 | 395 | −3.7 |
| 2B | 500 | 347 | 375 | 351 | −6.4 |
| 3A | 100 | 347 | 383 | 344 | −10.2 |
| 3B | 100 | 350 | 410 | 326 | −20.5 |
| 4A | 50 | 371 | 406 | 371 | −8.6 |
| 4B | 50 | 376 | 416 | 385 | −7.5 |
| 5A | 10 | 388 | 434 | 368 | −15.2 |
| 5B | 10 | 370 | 444 | 399 | −10.1 |
| 6A | 5 | 437 | 515 | 443 | −14.0 |
| 6B | 5 | 394 | 498 | 394 | −20.9 |
| 7A | 1 | 418 | 498 | 178 | −64.3 |

TABLE 5-continued

| Sample | Rab.IgG Amount | Starting R | R After Gold | R After Silver | % Change |
|---|---|---|---|---|---|
| 7B | 1 | 392 | 480 | 99 | −79.4 |

Figure 14:
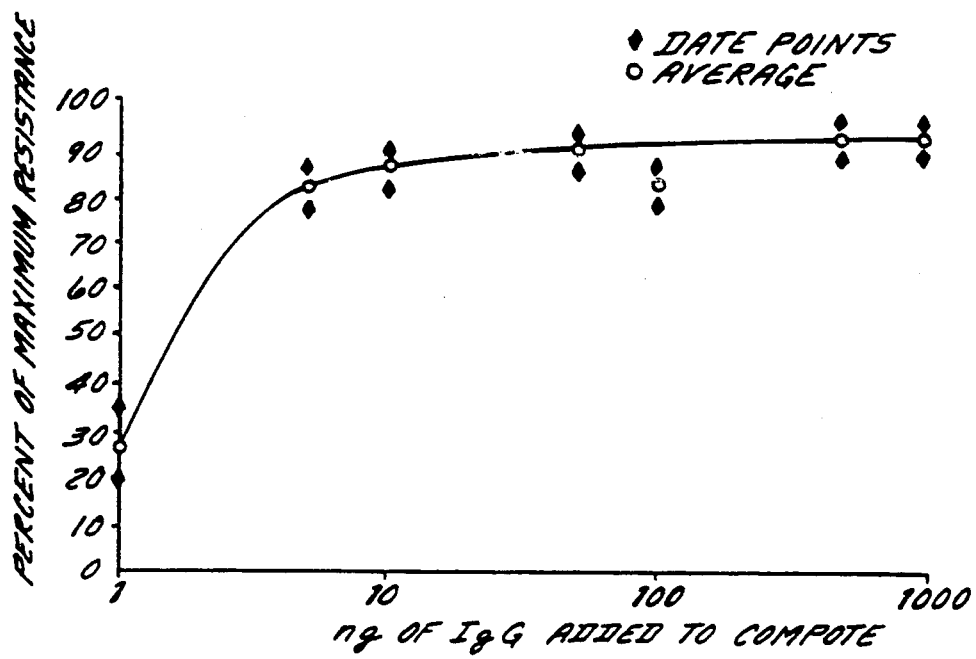
FIG. 14 is a graph wherein percent of maximum resistance determined in Example 5 is plotted against amount of competing antigen.

FIG. 14 graphically depicts a plot of percent of maximum resistance (100% minus percent change from Table 5 versus the amount of competing antigen, using the average of the two results A,B obtained for each amount of antigen plotted. The results indicate that the method of this example was sensitive enough to detect as little as 1 nanogram of antigen in a sample.

The procedures set forth in the foregoing examples may also be used to prepare other useful devices which need to have a bioreactive surface, for example, a bioimplant medical device such as an artificial heart or prosthetic part. In particular, the biocompatability of a metal implant can be improved by providing it with a thin coating of a bioreactive substance according to the invention, such as bioreactive plastic or chromium oxide. A layer of the recipient's own tissue may then bind to the bioreactive layer. The resulting device has a surface which can bind more firmly to the surrounding tissue and which is less likely to be rejected.

It will be understood that the above description is of preferred exemplary embodiments of the present invention, and the invention is not limited to the specific forms shown. The method of the invention is not limited to measuring or detecting an unknown quantity of a substance in a patient sample. It can also be used in research when it is desired to measure features of a binding reaction between two known substances, for example, the speed or extent of the reaction, or to construct a table of standard values for later use in analyzing a patient sample. These and other modifications may be made in the design of the invention without departing from the scope of the present invention as expressed in the appended claims.

We claim:

1. A diagnostic element for use in detecting a reaction between first and second members of a specific binding pair, wherein the second member of the specific binding pair is conductively labeled, said diagnostic element comprising:
    an electrically resistive support;
    an electrically resistive layer superposed on said support, the electrically resistive layer being made of a substance other than a member of the specific binding pair and which is capable of binding with one of the members of the specific binding pair;
    a pair of electrical conductors superposed side-by-side on the support and spaced apart to define a channel therebetween, said resistive layer defining a path which spans the conductors;
    wherein the path has a length effective for permitting resistive shunting of current between the conductors along the path, such that current can pass alternatively through the resistive layer and the conductively labeled member of the specific binding pair when the first and second members of the specific binding pair are disposed on the resistive layer.

2. The diagnostic element of claim 1, wherein said members of the specific binding pair comprise an antigen and an antibody.

3. The diagnostic element of claim 1, wherein said path has a resistance in a dry state in the range of about $10^3$ to $10^6$ ohms-cm, and said conductors have a resistance in a dry state of less than about 100 ohms-cm.

4. The diagnostic element of claim 1, wherein said resistive layer comprises a coating formed by sputter deposition.

5. The diagnostic element of claim 1, wherein said conductors comprise a pair of layers disposed side-by-side on said support, and said path comprises a channel having a width in the range of about 0.1 to 100 microns, said width being the distance between said conductive layers.

6. The diagnostic element of claim 5, wherein said electrically conductive layers consist essentially of a conductive metal and have thicknesses no greater than about 5 microns.

7. The diagnostic element of claim 1, wherein said support comprises a glass plate, and said resistive layer consists essentially of a composition selected from metal oxides, nitrides, oxynitrides, and combinations thereof.

8. The diagnostic element of claim 1, wherein said resistive layer consists essentially of chromium oxide.

9. The diagnostic element of claim 1, wherein said resistive layer consists essentially of carbon.

10. The diagnostic element of claim 1, wherein said members of the specific binding pair comprise proteins or nucleotides.

11. The diagnostic element of claim 1, wherein said path has a length of up to 1 cm.

12. The diagnostic element of claim 1, wherein said resistive layer comprises a cermet material.

13. The diagnostic element of claim 1, wherein one member of the specific binding pair is a microorganism.

14. The diagnostic element of claim 1, wherein one member of the specific binding pair is a portion of a microorganism.

15. The diagnostic element of claim 1, wherein one member of the specific binding pair is a hormone.

16. The diagnostic element of claim 1, wherein one member of the specific binding pair is an allergen.

17. The diagnostic element of claim 1, wherein one member of the specific binding pair is an enzyme.

18. The diagnostic element of claim 1, wherein one member of the specific binding pair is a steroid.

19. The diagnostic element of claim 1, wherein one member of the specific binding pair is a nucleotide.

20. The diagnostic element of claim 1, wherein one member of the specific binding pair is a drug.

* * * * *